United States Patent [19]

Day et al.

[11] Patent Number: 4,820,640

[45] Date of Patent: Apr. 11, 1989

[54] METHOD OF PRODUCING DEXTRANASE

[75] Inventors: Donal F. Day; David W. Koenig, both of Baton Rouge, La.

[73] Assignee: Louisiana State University and Agriculture and Mechanical College, Baton Rouge, La.

[21] Appl. No.: 837,839

[22] Filed: Mar. 10, 1986

[51] Int. Cl.$^4$ .................. C12N 9/46; C12N 1/16; C12R 1/645
[52] U.S. Cl. ................... 435/211; 435/255; 435/911
[58] Field of Search .................. 435/211, 255

[56] References Cited

PUBLICATIONS

Kreger-Van Rij ed., The Yeasts pp. 47, 48, 259, 260 (1984).
Webb et al., in Canadian Journal of Microbiology vol. 29 pp. 1092–1095 (1983).
Laires et al. in Zeitschrift Für Allgemeine Mikrubiologie vol. 23 (9) 601–603 (1983).

Primary Examiner—Lionel M. Shapiro
Attorney, Agent, or Firm—James M. Pelton

[57] ABSTRACT

A method of culturing Lipomyces, such as *Lipomyces starkeyi*, at pH of 2.5–4.5 and producing extracellular dextranase with co-production of alpha-glucosidase so that the dextranase containing product is essentially free from contamination.

6 Claims, 2 Drawing Sheets

FIG. 3
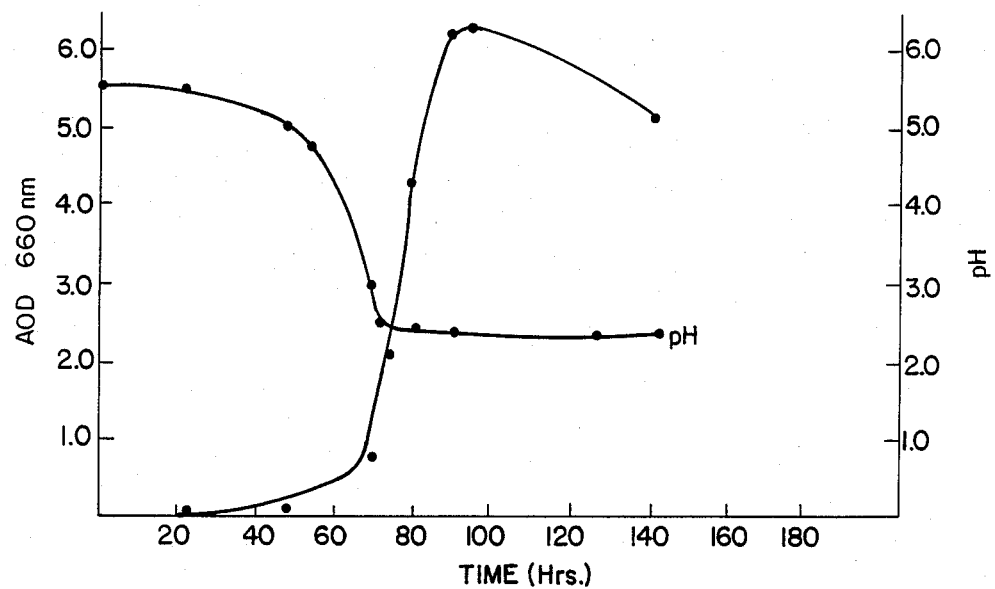
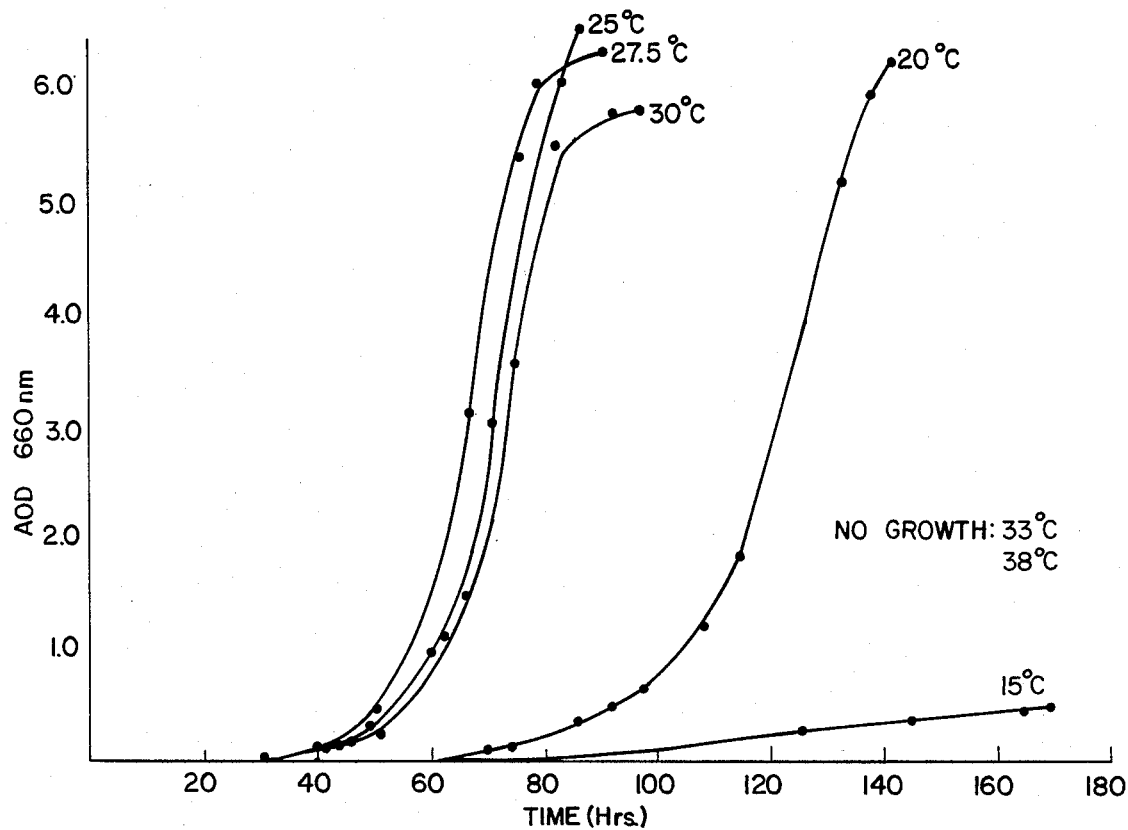
FIG. 4

METHOD OF PRODUCING DEXTRANASE

This invention relates to an improved method for producing dextranase, an enzyme capable of degrading dextran. More particularly this invention relates to an improved method which provides a dextranase product essentially free of biological contaminants.

Dextranase is used to hydrolyze dextran found in cane sugar production allowing the processing of previously unusable sugar juice for the production of sucrose. Dextranase has also been employed for the production of a dextran product which has found use as a blood substitute or extender. Because of its ability to hydrolyze dextran, dextranase has also been found highly useful for hydrolyzing the dextran produced by action of microorganisms causing dental caries or tooth decay. Thus, the incorporation of dxtranase into a tooth powder, toothpaste or other oral detergent is considered in the art to provide a preventative or curative for tooth decay.

There are many known microorganisms capable of producing dextranase including moulds, e.g. fungi belonging to the genera *Penicillium, Asperqillus, Spicaria, Fusarium* and *Chaetomium;* bacteria, e.g. *Lactobacillus, Cellvibrio, Flavobacterium* and the like, see for example, U.S. Pat. Nos. 2,742,399; 3,663,371; 3,875,009; and 3,912,594. In addition, it has also been reported that certain strains of yeasts have activity for dextranase, particularly strains of *Lipomyces starkeyi,* Webb and Spencer-Martins, Canadian Journal of Microbiology, Vol. 29, pages 1092–1095, 1983. However, this yeast has not been considered for industrial production of dextranase because of the reported slow growth of the organism and difficulty of avoiding contamination from other microorganisms during growth. This organism appears to be essentially acceptable under FDA procedures and, hence, useful in food industry dextranase applications.

In view of this, an object of the present invention is a method for culturing Lipomyces under unique conditions favoring rapid growth and low possibility of contamination by other microorganisms. Another object of this invention is a method for producing dextranase under conditions indicated by the prior art to be unproductive on an industrial scale. A further object of this invention is a dextranase product which is produced under conditions essentially free from biological contamination. These and other objects will be more fully illustrated in the following description of the invention.

THE INVENTION

This invention provides a method for culturing a yeast of the genus Lipomyces which comprises culturing said yeast at a pH in the range of about 2.5–4.5 in the presence of an assimilable carbon source. This invention also provides a method for producing a dextranase product comprising culturing a dextranase producing strain of Lipomyces or a mutant or variant of said dextranase-producing strain in a culture medium and recovering from said medium the dextranase which accumulates therein. Thus, a preferred method of this invention includes producing a dextranase product comprising cultivating an extracellular dextranase-producing strain of a microorganism identified as *Lipomyces starkeyi* ATCC No. 12659 in a medium containing dextran and simple salts for 36 to 72 hours at a pH within the range of about 2.5–4.5 and separating the vegetative cells from the culture medium thereby producing a dextranase-containing culture filtrate. This invention also pertains to the dextranase product which consists essentially of the dextranase-containing culture supernate substantially free from biological contaminants produced by the method described hereinabove.

DESCRIPTION OF THE DRAWINGS

The method of the present invention will be more fully understood by reference to the figures of the accompanying drawings in which

FIG. 3 is a graphical representation of the effect of pH on growth of *Lipomyces starkeyi* ATCC 12659 cells producing dextranase; an FIG. 4 is a graphical representation of the effect of temperature on growth of *Lipomyces starkeyi* ATCC 12659.

DESCRIPTION OF PREFERRED EMBODIMENTS OF THE INVENTION

Figure 1:
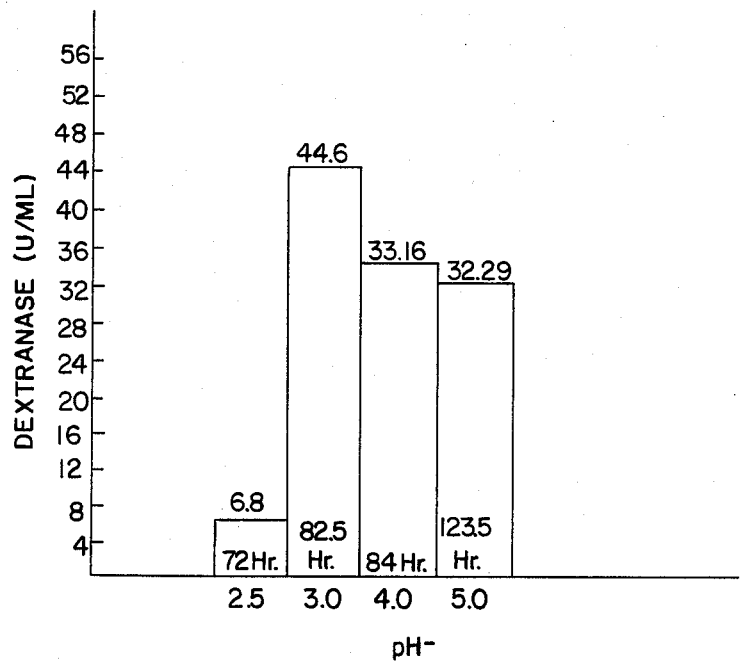
FIG. 1 is a bar graph representation of dextranase production as a function of pH.

Although some strains of Lipomyces have been known to produce dextranase, it has been found that *Lipomyces starkeyi* ATCC 12659 has a reduced lag time and grows well at lower pH and preferably in the highly acid pH range; more preferably between about pH 2.5–4.5. This feature of the invention provides industrial acceptability because of the possibility of contamination-free production in this pH range. By the terms "contamination-free" or "biologically contamination free" is meant that the conditions are much more favorable for growth of the Lipomyces than for other microorganisms; thus, at an acid pH range, most preferably of pH 2.5–4.5 very few microorganisms propagate at a rate sufficient to attain a concentration great enough to cause contamination problems.

Although the invention is not limited to this particular strain, a preferred strain, *Lipomyces starkeyi* ATCC 12659, was first identified from soil by R. L. Starkey, Journal of Bacteriology, Vol. 51, page 33 (1946). It was generally described by Lodder and Kreger-Van Rij in 1952, see H. J. Phaff and C. P. Kurtzman, *The Yeasts: A Taxonomic Study,* Ed. N. J. W. Kreger-Van Rij, 1984, Elsevier Publishers, Amsterdam, pages 259–260, which description is hereby incorporated by reference as if fully set forth. The yeast strain also has identification from other depositories, viz. NRRL Y-1389 and CB-1807 (Starkey's strain 74). In addition, other strains are known from the ATCC catalog and from previous publications, see Webb and Spencer-Martins, supra.

According to the present invention an organism of the genus Lipomyces capable of producing dextranase, particularly for example, such as *Lipomyces starkeyi* ATCC 12659, is cultured in a medium containing dextran or other carbon sources and a source of simple salts for about 2 to about 4 days. At the end of the culture period the vegetative cells may be separated and the culture medium may be used as a source of dextranase, e.g. such as in processes directed to hydrolyze dextran.

In carrying out the method of this invention in accordance with the best method known thereof, an aqueous nutrient fermentation medium is inoculated with a growing culture of the particular Lipomyces organism and the culture is then incubated under aerated conditions at a suitable temperature and pH. Typically the temperature is selected within the range of about 20° to about 30° C. Preferably, the temperature is controlled at about 27° C. and held thereat. The pH is controlled in an acid range preferably from about 3.0 to about 4.0.

The fermentation according to the present invention is carried out in a commercially available fermentation vessel. The culture medium is an aerated aqueous nutrient medium conventionally available, containing a source of assimilable carbon for growth and energy which preferably is also a suitable dextranase inducer and, more preferably, is dextran. Conventional minerals may also be added. A source of nitrogen is required for the production of dextranase. Preferably, a growth medium known as WW-DEX is used which contains the following:

| Reagent | Grams/Liter |
| --- | --- |
| Dextran (40,000 mol. wt.) | 10 |
| Potassium Phosphate, Monobasic | 2.5 |
| Ammonium Sulfate | 5.0 |
| Calcium Chloride | 0.1 |
| Sodium Chloride | 0.1 |
| Magnesium Sulfate | 0.1 |

The pH is adjusted with either HCl or NaOH, after sterilization, 1.0 ml of trace metals per liter are added. The trace metal stock has preferably the following composition:

| Reagent | Milligrams/Liter |
| --- | --- |
| Ferric Ammonium Sulfate | 14.00 |
| Zinc Sulfate Dihydrate | 3.00 |
| Manganese (II) Sulfate Tetrahydrate | 2.00 |
| Copper (II) Sulfate Pentahydrate | 0.30 |
| Ammonium Permolybdate | 0.09 |
| Boric Acid | 0.57 |

The trace metal stock is filter sterilized with a 0.2 micrometer filter.

It will be understood that the components of the nutrient medium can varied within known conventional limits and that the concentrations in which they are present can similarly be varied. Similarly, there can be supplemental additions or substitutions of any one of or a mixture of, for example, sugars such as sucrose, glucose and fructose and such variations together with variations in the mineral composition of the simple salts of the exemplified medium are well known in the art and are not further elaborated.

To provide oxygen for growth of the organism, the culture medium should be aerated during the incubation period. This can be achieved conveniently with the conventionally used aertion rate of between 0.25 and 1 liter of air per minute per liter of medium.

Suitably at least when using fermentation tanks the dissolved oxygen level can be monitored by means of a dissolved oxygen meter and the meter can be used to control the aeration rate as required by initiating a change in the degree of stirring of the medium or a change in the rate of air flow through the medium. Should either of these methods of aeration control lead to the production of excessive foam the situation can be rectified by the use of a mechanical foam breaker or, alternatively, the foam can be suppressed by addition of a conventional anti-foaming agent. When measurements indicate that a maximum concentration of dextranase has been reached in the culture medium the aeration and stirring are stopped. Since the dextranase is secreted extracellularly by the organism it accumulates in and is conveniently recoverable in the supernatant liquid obtained by settling the cells and decanting the supernatant culture medium. This supernatant liquid may then be concentrated by other means, for example, it can be concentrated by salting out with ammonium sulfate, alcohol precipitation or applying reverse osmosis, ultrafiltration, phase extraction or ion exchange techniques.

The dextranase produced according to the invention can be easily formulated into toothpaste or tooth powder, rubbing ointment or lotion, mouthwash, chewing gum, food, beverages and the like. Additionally, the dextranase product produced in accordance with this invention is capable of hydrolyzing dextran to give useful products such as monosaccharide glucose, the disaccharide isomaltose and higher oligosaccharides.

The activity of a particular enzyme, specifically dextranase, is analyzed or assayed for potency by reducing sugar production by the method of Nelson-Somogyi, see Journal of Biological Chemistry, vol. 160, p. 61 (1945). This method is carried out by incubating a 0.2 ml sample of the clarified culture supernate liquid with 0.6 ml deionized water, 1.0 ml of 2 percent T-2000 dextran (obtained from Pharmacia Company, Ltd., Uppsala, Sweden) and 0.05 molar citrate phosphate at pH 5.5 and at 50° C. Then 0.5 ml of this mixture is assayed at various time intervals for the reducing sugar content. A unit of dextranase activity is defined as the amount of enzyme which liberates 1.0 micro mole of glucose equivalents in ten minutes at the conditions described hereinabove.

It has also been found that the cells produced during the growth phase of the fermentation for the production of dextranase contained significant amounts of alpha-glucosidase. Thus, an additional feature of this invention is the co-production with dextranase of alpha-glucosidase which can be recovered from the washed cells according to known procedures. Some alpha-glucosidases are useful in starch conversion technology for production of sweeteners and alcohol, as an energy fuel or fuel additive. Alpha-glucosidase is assayed by collecting a known volume of culture supernate, removing the cells and concentrating or diluting with 0.1 molar phosphate buffer at pH 6.5. A sample of 0.8 milliliter is incubated at 30° C. and pH6.6 with 0.1 ml of 40 mg/ml of para-nitrophenyl-alpha-glucopyranoside from Sigma Chemical Company in 0.1 molar potassium phosphate buffer at pH 8. At predetermined time intervals 0.1 ml of 3.0 molar sodium carbonate is added to stop the reaction and develop the color. The suspension is clarified and the amount of nitrophenol liberated is measured at 420 nm by spectrophotometer. A unit of alpha-glucosidase is defined as the amount of enzyme required to liberate one micro mole of nitrophenol per minute under the conditions described above.

Alpha-glucosidase is co-produced by the dextranase producing strain of *Lipomyces starkeyi* ATCC 12659. The conditions for optimum production of alpha-glucosidase are the same as those for production of the dextranase. Accordingly, the optimization of the dextranase producing properties of this yeast strain will also optimize alpha-glucosidase production.

Having described the method of this invention, the following example will serve to further illustrate the method and describe the best mode known to the inventors for carrying out the method.

EXAMPLE

An inoculum is cultured on a medium containing WW-DEX as described hereinabove supplemented with 2.0 grams/liter of yeast extract. The inoculum culture has an optical density of 5.0–6.0 uncorrected at 660 nanometers against a water blank. Then 0.5 ml of this inoculum is added aseptically by a hypodermic syringe to a New Brunswick Microfirm Fermenter containing 500 ml of WW-DEX culture medium. The medium has been previously autoclaved in the fermenter vessel for 15 minutes at 121° C. and 15 psi. After cooling to 27° C., 0.5 ml of sterile trace metal solution is added. The pH control is maintained by using a 3.0 molar NaOH controlled drip as measured by an Ingold type pH electrode which was UV sterilized before being aseptically inserted into the vessel. Temperature is controlled by an external thermal regulator which monitors the temperature of the vessel and is capable of heating on demand. Cooling is accomplished by use of a coldfinger attached to an external refrigeration unit. A pyrex gas dispersion tube allows for uniform aeration. Agitation is accomplished with the use of a magnetic stirrer inside of the vessel controlled externally with a FisherVersamix stir plate. Sampling is accomplished by retrieving 15 ml aliquots from a sampling port at various time intervals. Time zero is designated as the initial injection of the inoculum into the vessel. The standard operating conditions for the fermentation experiments are stirring rate of 200 rpm, aeration rate of 0.5 liters per minute of air, pH controlled with 3.0 molar sodium hydroxide, temperature of 27° C., volume 500 ml of WW-DEX medium and 0.5 ml of the inoculum. These conditions are maintained except as required for various runs to investigate the prescribed parameters. The results of controlled pH experiment in which the pH was maintained at 2.5, 3.0, 4.0 and 5.0 are shown below in Tables I–IV.

TABLE I

Fermenter Run at pH 2.5 Controlled (NaOH)
500 ml, Aeration 0.5 liters/minute, Temperature 27° C.
Medium - WW-Dextran (Inds. Grade)
Inoc. 0.5 ml of OD (660 nm) = (1/10) 0.700

| Elapsed Time (H) | Cells per ml × $10^6$ | Alpha-glucosidase (Units/ml) × $10^{-4}$ | Dextranase Units/ml |
|---|---|---|---|
| 0 | ND* | — | — |
| 24 | ND* | 0.0456 | 0.044 |
| 47 | 3.166 | 0.334 | 0.016 |
| 58 | 41.910 | 0.0624 | 0.172 |
| 72 | 110.260 | 5.96 | 6.800 |
| 83 | 67.725 | 1.93 | 0.434 |
| 96.5 | 65.207 | 4.97 | ND* |

*Not Detected

TABLE II

Fermenter Run at pH 3.0 Controlled (NaOH)
500 ml, Aeration 0.5 liters/minute, Temperature 27° C.
Medium - WW-Dextran (Inds. Grade)
Inoc. 0.5 ml of OD (660 nm) = (1/10) 0.598

| Elapsed Time (H) | Cells per ml × $10^6$ | Alpha-glucosidase (Units/ml) × $10^{-4}$ | Dextranase Units/ml |
|---|---|---|---|
| 0 | ND* | ND | — |
| 11 | ND* | ND | ND |
| 21.75 | 0.01838 | — | — |
| 36.25 | 1.3336 | 0.0314 | 1.01 |
| 45.25 | 5.433 | 0.189 | 1.556 |
| 58.75 | 33.865 | 0.785 | 3.594 |
| 62.75 | 49.256 | 0.541 | 3.460 |
| 70.25 | 119.496 | 3.60 | 34.00 |
| 82.5 | 103.825 | 2.29 | 44.00 |
| 106.75 | 109.421 | 1.95 | 28.00 |

*Not Detected

TABLE III

Fermenter Run at pH 4.0 Controlled (NaOH)
500 ml, Aeration 0.5 liters/minute, Temperature 27° C.
Medium - WW-Dextran (Inds. Grade)
Inoc. 0.5 ml of OD (660 nm) = (1/10) 0.506

| Elapsed Time (H) | Cells per ml × $10^6$ | Alpha-glucosidase (Units/ml) × $10^{-4}$ | Dextranase Units/ml |
|---|---|---|---|
| 0 | ND* | — | — |
| 11.5 | ND* | ND | ND |
| 36 | 2.411 | 0.241 | 0.750 |
| 45.5 | 9.463 | 0.275 | 1.908 |
| 59.5 | 67.725 | 1.29 | 12.578 |
| 62.5 | 73.18 | — | — |
| 67 | 88.433 | 6.24 | 31.34 |
| 84 | 96.548 | 1.87 | 33.16 |

*Not Detected

TABLE IV

Fermenter Run at pH 5.0 Controlled (NaOH)
500 ml, Aeration 0.5 liters/minute, Temperature 27° C.
Medium - WW-Dextran (Inds. Grade)
Inoc. 0.5 ml of OD (660 nm) = (1/10) 0.506

| Elapsed Time (H) | Cells per ml × $10^6$ | Alpha-glucosidase (Units/ml) × $10^{-4}$ | Dextranase Units/ml |
|---|---|---|---|
| 0 | ND* | — | — |
| 18.5 | ND* | — | — |
| 41.5 | 0.3961 | 0.0284 | 0.946 |
| 64 | 2.551 | 0.0527 | 3.128 |
| 71.5 | 3.978 | — | — |
| 88 | 8.679 | 0.220 | 4.554 |
| 102 | 25.679 | 0.289 | 5.310 |
| 113 | 56.390 | 1.68 | 12.994 |
| 123.5 | 87.314 | 5.69 | 32.292 |
| 137 | 103.825 | 4.02 | 25.168 |
| 160.5 | 102.146 | 2.54 | 13.374 |

*Not Detected

Based on the above four experiments, the maximum dextranase production as a function of pH, as shown in FIG. 1, indicates a maximum dextranase activity of 6.8 at pH 2.5, 44.00 at pH 3, 33.16 at pH 4 and 32.29 at pH 5.

Figure 2:
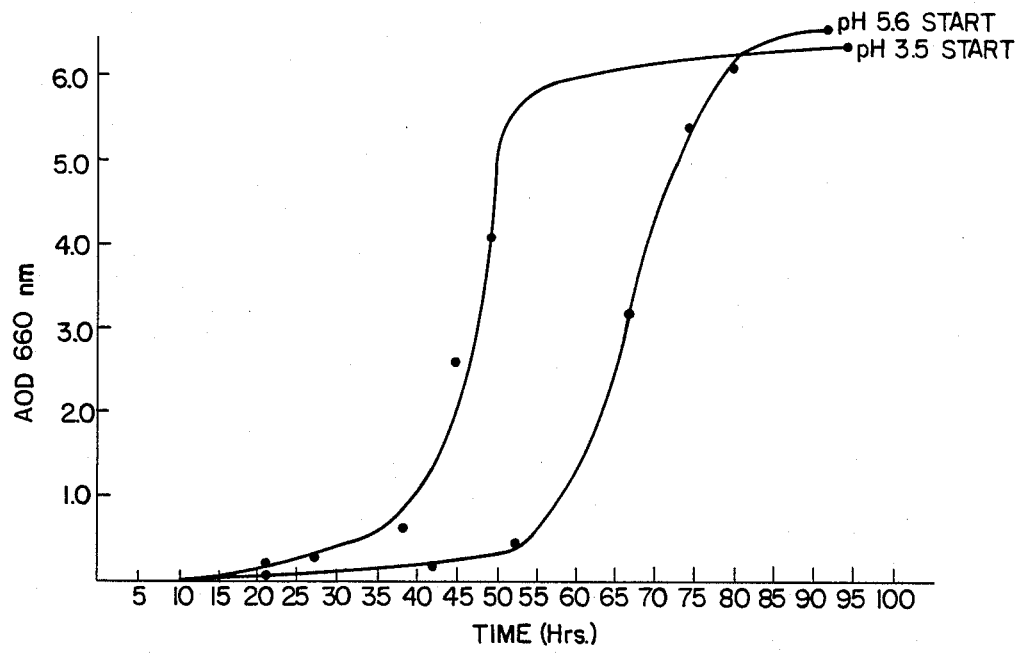
FIG. 2 is a graphical representation of the growth of cells in the culture medium at two different initial pH levels over time.

Comparative growth rate tests were run at an initial pH of 3.5 and an initial pH of 5.6, other conditions being the same. The results of the experiment show clearly, as seen in FIG. 2 that the experiment in which the pH was 3.5 had shorter lag time and a growth rate just as high as that of an initial pH of 5.6. Average time until exponential growth began was about 1.5 days (about 36 hours) whereas at an initial pH of 5.6 exponential growth started at over 2.25 days and did not reach stationary phase indicating completed growth until about 3.5 days whereas the stationary phase was about 2.25 days for the lower pH. This clearly shows that the lower pH has a shorter induction period or lag phase for this strain of *Lipomyces starkeyi*. As seen in FIG. 3, a plot of the cell growth versus time as compared with pH versus time, starting at an initial pH of 5.5 and decreasing the pH to about 2.5, growth increased when the pH began to decline to about 3.5 reaching the maximum growth in about 3.5 days (about 84 hours). This shows that the higher pH caused a greater induction time and that the growth phase was entered when the pH decreased.

FIG. 4 shows the effect of temperature on cell growth. Clearly the temperature range is between 20° and 30° C. since very slow growth at a long induction period occurred at 15° C. and no growth was shown at temperatures higher than 3° C.

The examples could be run on mutants of the foregoing specifically mentioned strain which are expected to produce results of at least an equally satisfactory nature. However, the above examples are sufficient to illustrate the efficacy of the invention. The foregoing description demonstrates that dextranase can be satisfactorily produced from *Lipomyces starkeyi* ATCC 12659 under conditions which are unexpected and indicated in the art to be less than satisfactory. In view of this, it is clear from the above description that skilled practitioners will recognize modifications or changes which can be made without departing from the scope or spirit of the present invention. Therefore it is desired that the invention be limited only by the lawful scope of the following claims.

We claim:

1. A method for producing an extracellular dextranase which comprises culturing a yeast of the genus Lipomyces at a controlled pH in the range of about 2.5 to 4.0 in the presence of an assimilable carbon source and separating the vegetative cells to produce a dextranase-containing culture supernate.

2. The method of claim 1 in which the culture medium contains dextran.

3. The method of claim 2 in which said culture medium contains simple salts.

4. The method of claim 1 in which the culturing is carried out at a temperature of from about 20° to about 30° C.

5. The method of claim 1 in which said Lipomyces is *Lipomyces starkeyi*.

6. The method of claim 5 in which said *Lipomyces starkeyi* is *Lipomyces starkeyi* ATCC No. 12659 and the culturing is carried out at a controlled pH in the range of about 3.0 to about 4.0 and at a temperature in the range of about 20° to about 30° C.

* * * * *